(12) United States Patent
Wen et al.

(10) Patent No.: US 6,989,896 B2
(45) Date of Patent: Jan. 24, 2006

(54) STANDARDIZED SAMPLE FOR CHARACTERIZING THE PERFORMANCE OF A SCATTEROMETER

(75) Inventors: Youxian Wen, Livermore, CA (US); Cheryl Staat, San Jose, CA (US); Jon Opsal, Livermore, CA (US)

(73) Assignee: Therma-Wave, Inc., Fremont, CA (US)

( * ) Notice: Subject to any disclaimer, the term of this patent is extended or adjusted under 35 U.S.C. 154(b) by 463 days.

(21) Appl. No.: 10/268,375

(22) Filed: Oct. 9, 2002

(65) Prior Publication Data

US 2005/0083520 A1    Apr. 21, 2005

Related U.S. Application Data

(60) Provisional application No. 60/366,731, filed on Mar. 22, 2002, provisional application No. 60/342,785, filed on Dec. 21, 2001, provisional application No. 60/329,900, filed on Oct. 16, 2001.

(51) Int. Cl.
    *G01J 1/10*    (2006.01)
(52) U.S. Cl. .................. 356/243.7; 356/243.1
(58) Field of Classification Search ... 356/243.1–243.8
    See application file for complete search history.

(56) References Cited

PUBLICATIONS

The Advanced Metrology Advisory Group (AMAG), "Reticle Design Description," by Sematech International, Feb. 2000, 11 pages in length.

*Primary Examiner*—Gregory J. Toatley, Jr.
*Assistant Examiner*—Amanda Merlino
(74) *Attorney, Agent, or Firm*—Stallman & Pollock LLP

(57) ABSTRACT

A standardized sample for scatterometry includes four quadrants each including an inner block surrounded by four outer blocks. A pattern of gratings is repeated within each of the blocks using different resolutions and orientations. Each grating within an outer block has a matching grating within the block's pair. A grating and its matching grating are negative images of each other—the pitch and line-size of a grating are equal, respectively to the line size and pitch of the matching grating. The inner block also includes a series of background patterns positioned behind the gratings. These patterns include repeating patterns of hole and repeating line structures. This series of structures cover a large die area, helping to simulate the conditions faced by real-world scatterometers. The various structures feature a high-degree of alignment, allowing rapid verification using SEM or other techniques.

5 Claims, 14 Drawing Sheets

Fig. 17a
Reflectometer

Fig. 21a
Reflectometer

STANDARDIZED SAMPLE FOR CHARACTERIZING THE PERFORMANCE OF A SCATTEROMETER

PRIORITY CLAIM

The present application claims priority to U.S. Provisional Patent Applications Ser. No. 60/329,900, filed Oct. 16, 2001, Ser. No. 60/366,731, filed Mar. 22, 2002, and Ser. No. 60/342785 filed Dec. 21, 2001 all of which are incorporated herein by reference.

TECHNICAL FIELD

The subject invention relates to standardized samples used during the evaluation of scatterometers, reflectometers, ellipsometers and other optical metrology systems.

BACKGROUND OF THE INVENTION

As geometries continue to shrink, manufacturers have increasingly turned to optical techniques to perform non-destructive inspection and analysis of semi-conductor wafers. The basis for these techniques is the notion that a subject may be examined by analyzing the reflected energy that results when a probe beam is directed at the subject. Ellipsometry and reflectometry are two examples of commonly used optical techniques. For the specific case of ellipsometry, changes in the polarization state of the probe beam are analyzed. Reflectometry is similar, except that changes in magnitude are analyzed. Ellipsometry and reflectometry are effective methods for measuring a wide range of attributes including information about thickness, crystallinity, composition and refractive index. The structural details of ellipsometers are more fully described in U.S. Pat. Nos. 5,910,842 and 5,798,837 both of which are incorporated in this document by reference.

Scatterometry is a related technique that measures the diffraction (optical scattering) that results when a probe beam is directed at a subject. Scatterometry is an effective method for measuring the critical dimension (CD) of structural features (such as the lines and other structures included in integrated circuits). Scatterometry can be used to analyze periodic two-dimensional structures (e.g., line gratings) as well as periodic three-dimensional structures (e.g., patterns of vias or mesas in semiconductors). Scatterometry can also be used to perform overlay registration measurements. Overlay measurements attempt to measure the degree of alignment between successive lithographic mask layers.

Figure 1:
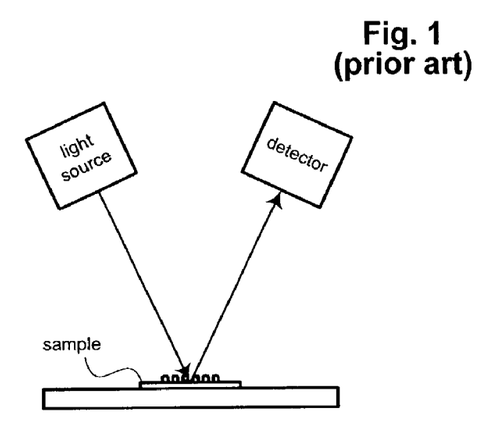
FIG. 1 is a block diagram of a prior art scatterometer.

As shown in FIG. 1, a typical scatterometer generates a probe beam using an illumination source. Depending on the type of scatterometer, the illumination source may be mono or polychromatic. The probe beam is directed at a subject to be analyzed. The subject includes a periodic structure such as a grating. The reflected probe beam is received by a detector. Once received, changes in reflectivity or polarization state of the probe beam are measured as a function of angle of incidence or wavelength (or both). These changes are used to analyze the subject.

Figure 2:
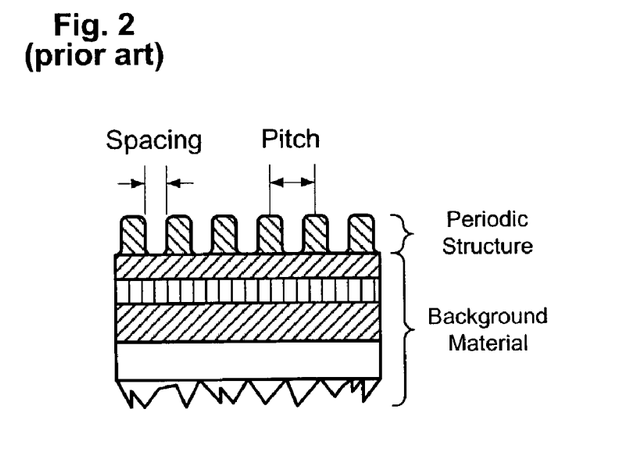
FIG. 2 is a block diagram of a prior art film stack shown as a generic scatterometry subject.

Scatterometry may be used to analyze a wide range of different subjects. As shown in FIG. 2, a typical subject includes a periodic structure overlaying a background material. The background material is typically (for the case of semi-conductor wafers) a multilayer dielectric film. The periodic structure may be composed of one or more layers. For a typical analysis, a scatterometer may be used to measure a range of features of the periodic structure including line size, line spacing, line pitch, and line height. Line shape and side wall profiles may also be characterized.

The value of scatterometry systems is entirely dependent on their accuracy. Accuracy, in turn, is generally dependent on proper calibration of all involved systems. Unfortunately, proper scatterometer calibration is not entirely straightforward. In practice, calibration is often measured by comparing scatterometry results to the results obtained by an alternate method, such as a scanning electron microscope (SEM). This process is somewhat painstaking—requiring that test subjects be partitioned using a saw or other device to expose their critical features. Comparison to devices such as the SEM is also not without its own errors—there are cases where the scatterometer produces results that exceed the accuracy of the SEM.

In some cases, a specially prepared subject, known as a standardized sample is used to perform scatterometer calibration. Standardized samples have known features (often because they have been pre-measured using an atomic force microscope or other device). In theory, this allows scatterometers to be quickly and accurately calibrated by observing the result obtained during inspection of a standardized sample. In practice, this is not always the case. This is true largely because the standardized samples generally fail to provide adequate coverage of the features and conditions that are encountered during actual use of scatterometers in production environments.

For example, it is generally the case that the size of semi-conductor wafers continues to increase. Scatterometers and other inspection equipment must be calibrated to produce accurate measurements at all points within these increasingly large objects. This is true even where the optical components of the scatterometer are configured to remain stationary and the subject is moved to inspect different locations. Semi-conductor wafers also include a wide range of different structures at different orientations. A single wafer, for example, will typically include lines having different sizes, pitches and other important aspects. For optimal performance, each different structure must be accounted for during calibration.

Semi-conductor wafers (and other subjects) are produced using a wide range of layers, composed of a wide range of materials and arranged in a wide range of thicknesses and permutations. Since the accuracy of the scatterometry process may be influenced by these different configurations, it is important that they be accounted for during the calibration process. In practice, this is a particularly difficult part of the calibration process, since the range of possible configurations is nearly limitless.

To some extent, the dielectric properties of semi-conductor wafers tend to change over time. This is especially true for layers fabricated using organic materials. Exposure to light, especially in the UV range, causes chemical changes in the layers. The aging process also affects the standardized samples constructed to calibrate scatterometers and other optical metrology systems. This is problematic because the line/space features included in standardized samples are typically characterized at the time of their manufacture. Over time, the aging process causes the results to change introducing errors into the calibration process.

In production environments, calibration must also be accomplished quickly with minimal setup time. Calibration must also be performed under a range of different test conditions (such as varying temperature).

All of these factors contribute to the complexity of scatterometer calibration. And while some of them have been at least partially met by existing standardized sample solutions, no current standardized sample provides a comprehensive solution. For at least these reasons, there is a continuing need for better calibration techniques for scatterometers and related optical inspection systems.

SUMMARY OF THE INVENTION

The present invention includes a standardized sample for evaluation and calibration of scatterometry equipment. For a representative embodiment, the standardized sample has a square or rectangular shape that is conveniently described using X and Y Cartesian coordinates. Typically, the square shape of the standardized sample is subdivided into four quadrants. Each quadrant is further subdivided into five blocks—an inner block and four outer blocks. The four outer blocks are grouped into two pairs: a vertical pair and a horizontal pair.

Each outer block includes a series of gratings, each having a different pitch and line size. The gratings within the vertical pair of blocks are aligned vertically—with lines parallel to the y-axis. The gratings within the horizontal pair of blocks are aligned horizontally—with lines parallel to the x-axis. Each grating within an outer block has a matching grating within the block's pair. A grating and its matching grating are negative images of each other—the pitch and line-size of a grating are equal, respectively to the line size and pitch of the matching grating.

The inner block includes an additional series of gratings. The inner block also includes a series of background patterns positioned behind the gratings. These patterns include repeating patterns of hole and repeating line structures.

This series of structures cover a large die area, helping to simulate the conditions faced by real-world scatterometers. The various structures feature a high-degree of alignment, allowing rapid verification using SEM or other techniques.

The standardized sample is created by etching a multi-layer dielectric film stack. Preferably, the film stack is created to resist age and exposure related changes in dielectric properties. For a typical case, the stabilized film stack is created to mimic the dielectric properties of a production film stack. Effective layers are defined to replace the aging-prone layers of the production film stack. Each effective layer is an age resistant combination of one or more layers that mimics the dielectric response of an aging-prone layer in the production film stack. For organic anti-reflective coatings and organic photo resist materials, equivalent effective layers are often defined using inorganic materials (SiON and $SiO_2$, respectively). The stabilized film stack is then created as a combination that includes the effective layers and replicates the age-resistant layers from the production film stack. The age resistant film stack is then etched to create the line/space features. Alternately, it is also possible to forego the etching process and use the age resistant film stack as a stabilized sample for calibration and testing of ellipsometers and reflectometers.

DETAILED DESCRIPTION OF THE PREFERRED EMBODIMENTS

Figure 3:
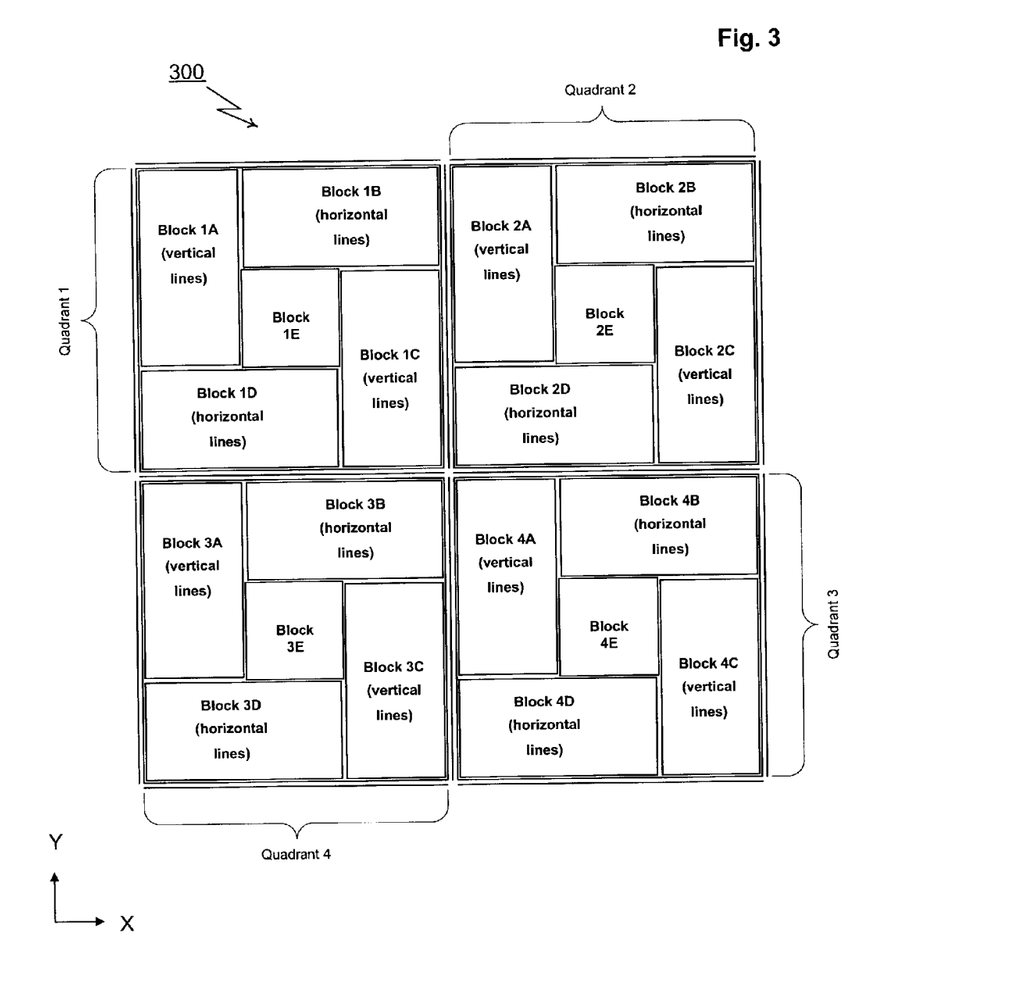
FIG. 3 is a block diagram of an embodiment of the standardized sample of the present invention.

The present invention includes a standardized sample that may be used for evaluation and calibration of scatterometry equipment. As shown in FIG. 3, a representative embodiment of the standardized sample 300 has a square or rectangular shape that is conveniently described using X and Y Cartesian coordinates. Standardized sample 300 is typically subdivided into four equal-sized quadrants (labeled 1 through 4 in FIG. 3). Each quadrant is a square 1.24 cm by 1.24 cm making the entire standardized sample 2.5 cm square. Each of these dimensions may be varied to suit the needs of particular applications.

Each quadrant is further subdivided into five blocks—an inner block and four outer blocks. In FIG. 3, the inner blocks are labeled by their quadrant number followed by the letter E (1E, 2E, 3E and 4E). The outer blocks are labeled with their quadrant number followed by one of the letters A through D (e.g., 1A or 3B).

Figure 4:
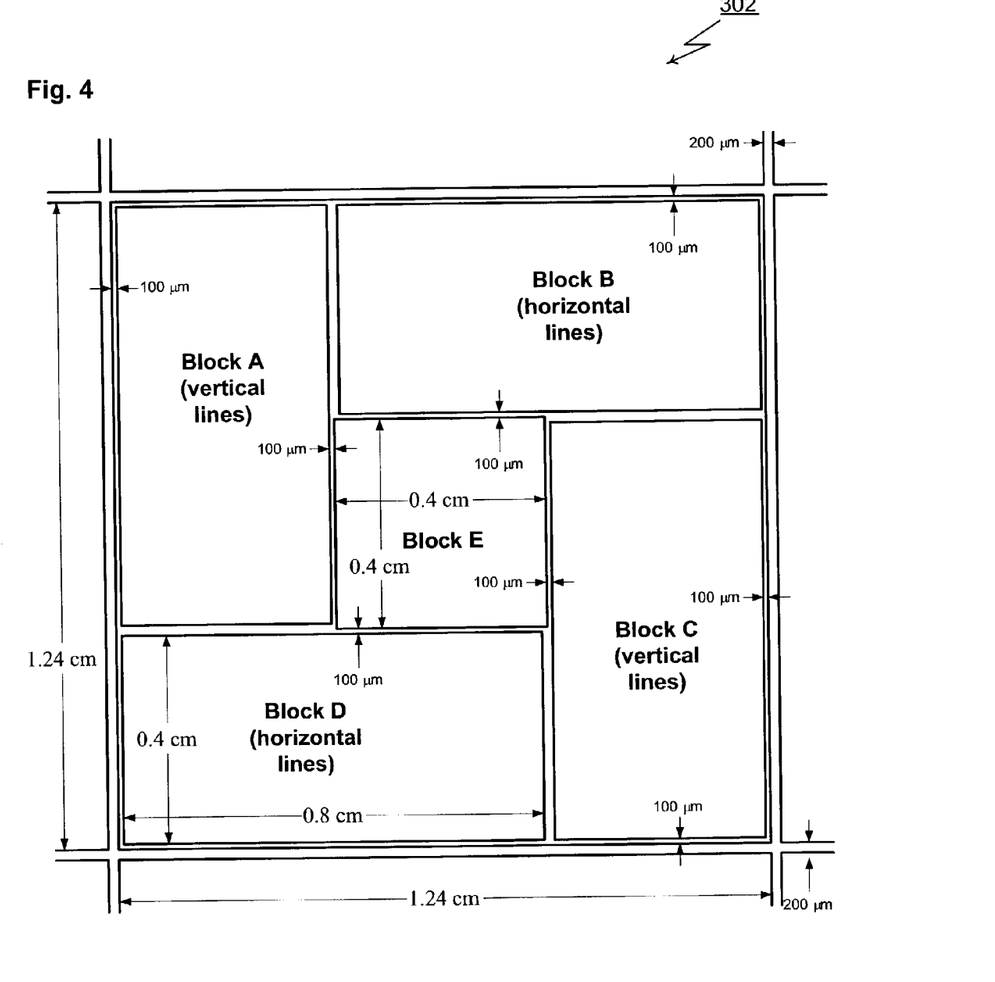
FIG. 4 is a block diagram of a quadrant of the standardized sample of FIG. 3.

As shown more clearly in FIG. 4, the four outer blocks in each quadrant are grouped into two pairs: a vertically oriented pair including blocks A and C and a horizontally oriented pair including blocks B and D. For this particular example, the vertically oriented blocks (A and C) are 0.4 cm long in the X dimension and 0.8 cm long in the Y dimension. The horizontally oriented blocks (B and D) are 0.8 cm long in the X dimension and 0.4 cm long in the Y dimension. The inner block (E) is 0.4 cm by 0.4 cm.

Figure 5:
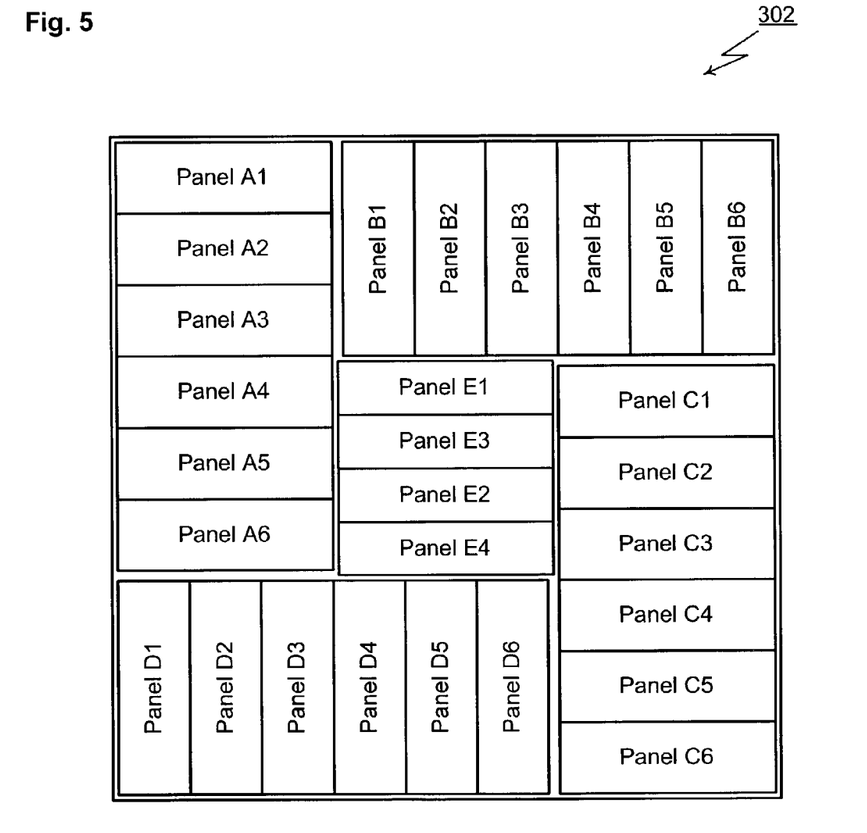
FIG. 5 is a block diagram showing the panels included in the quadrant of FIG. 4.
Figure 6:
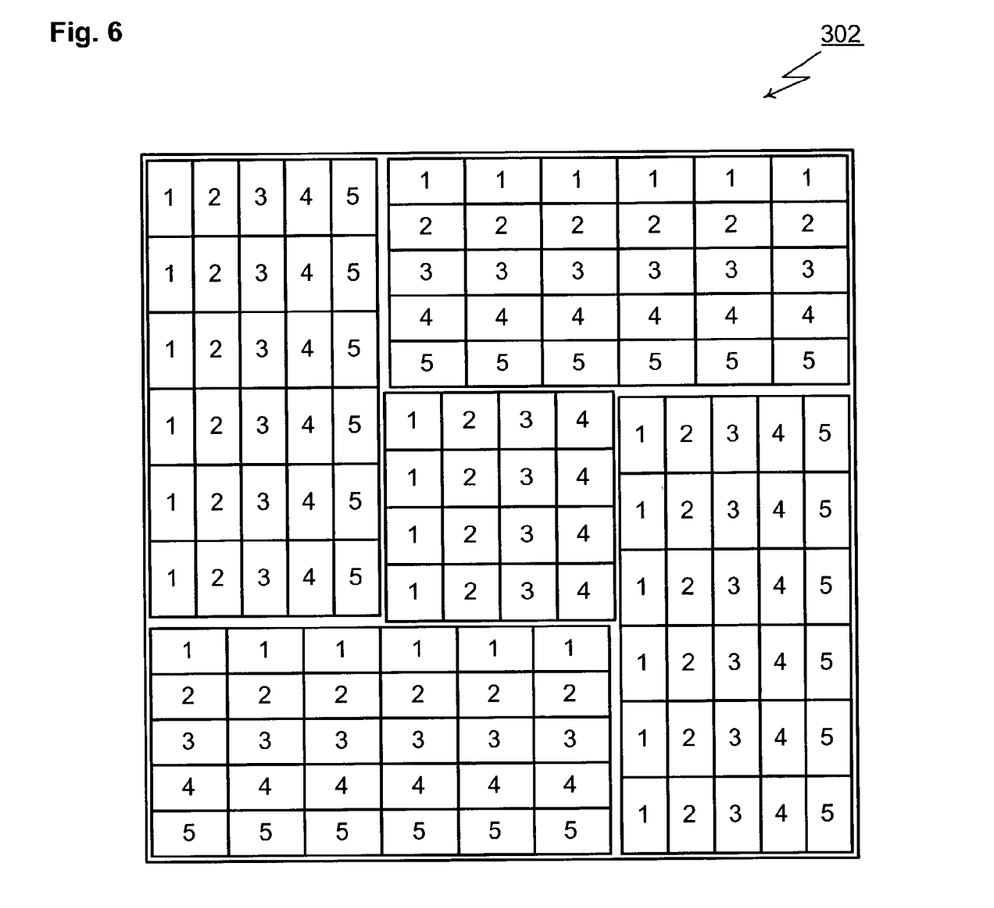
FIG. 6 is a block diagram showing the test regions included in the panels of FIG. 5.

Each quadrant is divided into a series of panels as shown in FIG. 5. The outer blocks A through D include six panels. The inner block E includes four panels. Each of these panels is further subdivided into a series of test regions. As shown in FIG. 6, each of the panels within the outer blocks A through D includes five test areas. This gives each outer block a total of thirty test regions. Each of the panels within the inner block E includes four test regions giving inner block E a total of sixteen test regions.

Figure 7:
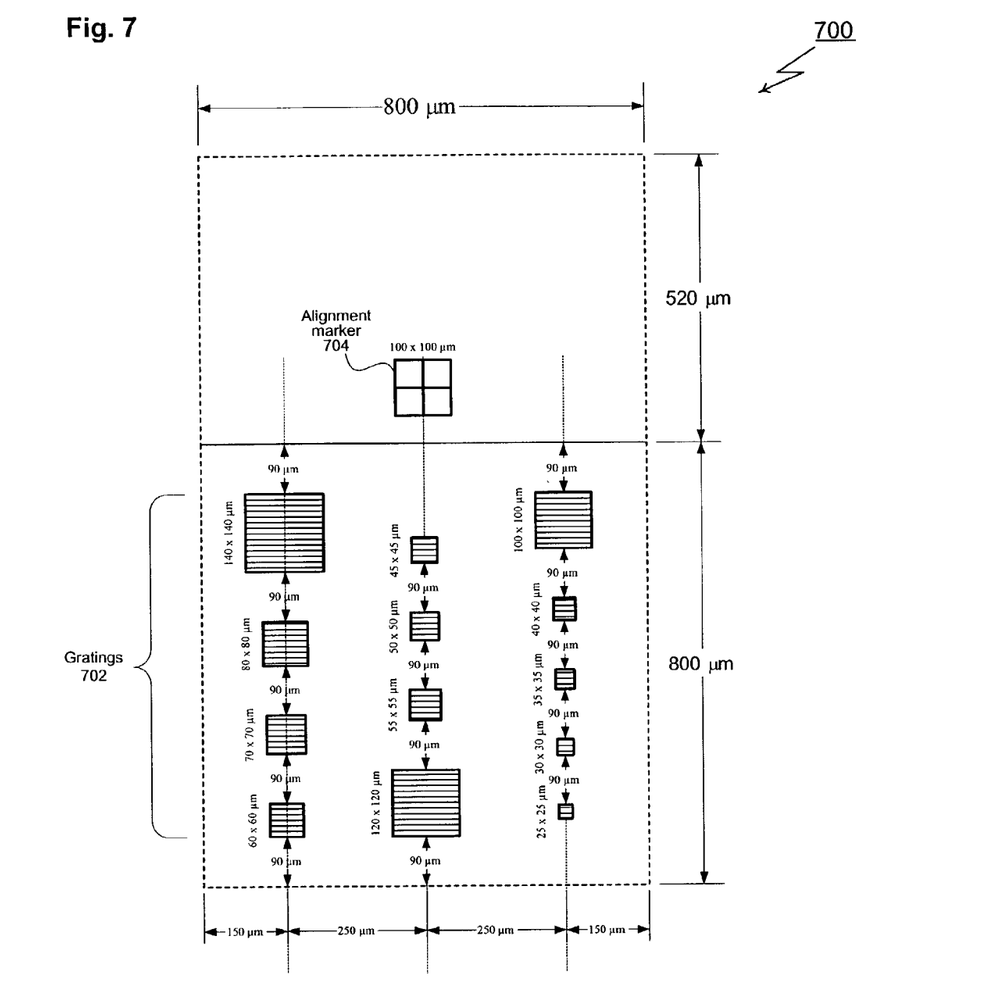
FIG. 7 is a block diagram of the foreground pattern used within the test regions shown in FIG. 6.
Figure 8:
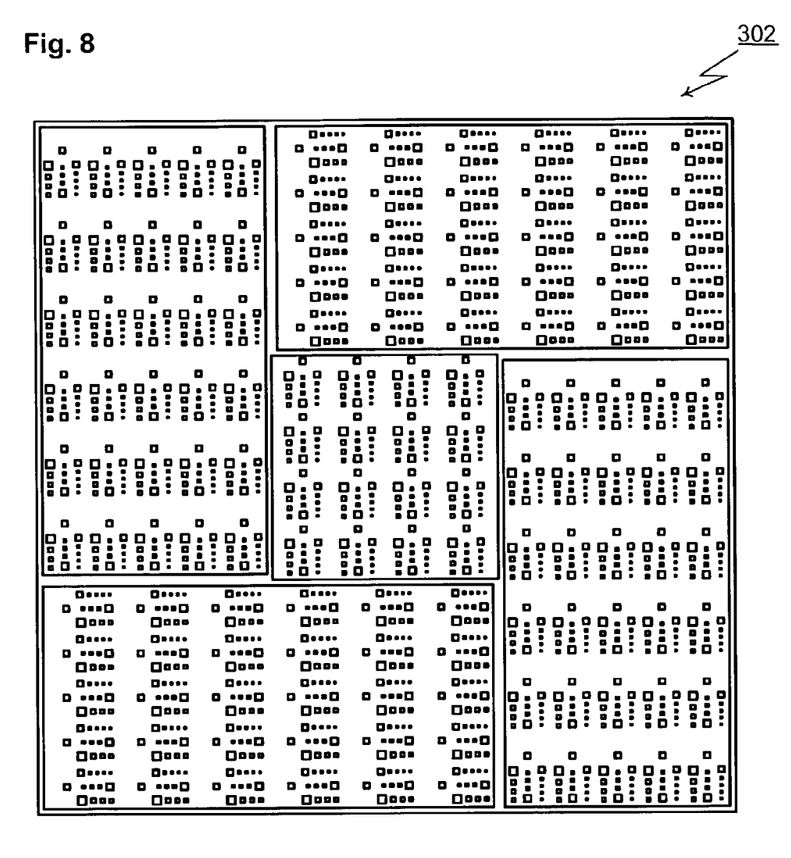
FIG. 8 is a block diagram showing the foreground pattern of FIG. 7 applied to the test regions shown in FIG. 6.

Each test regions includes the foreground pattern 700 shown in FIG. 7. The foreground pattern includes is a series of thirteen square gratings 702. Each grating 702 has a different size. For the particular example shown this includes 25 μm, 30 μm, 35 μm, 40 μm, 45 μm, 50 μm, 55 μm, 60 μm, 70 μm, 80 μm, 100 μm, 120 μm, and 140 μm gratings 702. The size of each grating is printed to the grating's left. For the example being described, the printing is 10 μm tall and is spaced 20 μm from the associated grating. The foreground pattern 700 also includes an alignment marker 704. The alignment marker 704 is a 100 μm by 100 μm box that includes a pair of crossed, perpendicular lines. FIG. 8 shows a representative implementation of a quadrant 302 with the foreground pattern 700 repeated in each test region.

The same pitch is used for each of the thirteen gratings 702 within a given test region. A single pitch is also used for each of the test regions included in a given panel. This means, for example that each of the gratings within the four test regions of the first panel of the inner block has a 1000 nm pitch. The pitches used within each panel (and each included test region and grating) are summarized in the following table:

|   | Panel 1 | Panel 2 | Panel 3 | Panel 4 | Panel 5 | Panel 6 |
|---|---------|---------|---------|---------|---------|---------|
| 1E | 1000 nm | 800 nm | 700 nm | 600 nm | N/A | |
| 2E | 500 nm | 400 nm | 300 nm | 200 nm | | |
| 3E | 500 nm | 400 nm | 300 nm | 200 nm | | |
| 4E | 1000 nm | 800 nm | 700 nm | 600 nm | | |
| 1A ... 1D | 1500 nm | 1400 nm | 1200 nm | 1000 nm | 900 nm | 800 nm |
| 2A ... 2D | 1500 nm | 1400 nm | 1200 nm | 1000 nm | 900 nm | 800 nm |
| 3A ... 3D | 700 nm | 600 nm | 500 nm | 400 nm | 300 nm | 200 nm |
| 4A ... 4D | 700 nm | 600 nm | 500 nm | 400 nm | 300 nm | 200 nm |

As shown in this table, a wide range of pitches are included starting at 200 nm and extending to 1500 nm.

As discussed, the same pitch is used for each grating within a given panel. The line size and line spacing is not, however, held constant within any panel. Instead, the panels are configured so that each test area has a different line space and line size. For the first panel of the inner block E this means that the test regions have line spaces of 1:1, 1:2, 1:3 and 1:5, respectively. The line spaces and line sizes used within each test region of each panel are summarized in the following table:

|   | Test Region 1 | Test Region 2 | Test Region 3 | Test Region 4 | Test Region 5 |
|---|---|---|---|---|---|
| 1B, 1C, 2B, 2C | L:S = 1:1 | L:S = 1:2 | L:S = 1:3 | L:S = 1:4 | L:S = 1:5 |
| 1A, 1D, 2A, 2D | L:S = 5:1 | L:S = 4:1 | L:S = 3:1 | L:S = 2:1 | L:S = 1:1 |
| 3B, 3C, 4B, 4C | L:S = 1:6 | L:S = 1:7 | L:S = 1:8 | L:S = 1:10 | Film stack |
| 1A, 1D, 2A, 2D | L:S = 10:1 | L:S = 8:1 | L:S = 7:1 | L:S = 6:1 | Film stack |
| 1E, 2E, 3E, 4E | L:S = 1:1 | L:S = 1:2 | L:S = 1:3 | L:S = 1:5 | N/A |

As shown in this table, blocks B and C (in all quadrants) may be described as light fields. In these blocks line sizes are greater than, or equal to line spacings. Blocks A and D (in all quadrants) are dark fields—line spacings are greater than, or equal to line sizes. This subdivision (of blocks into light and dark fields) splits the vertically oriented pair of blocks (A and C) into a conjugate pair including one light and one dark field. Each test region in either of these blocks (A or C) is a negative image of the same test region in the block's pair (A or C). In this context, negative image is meant to describe the situation where the line spacing a test region matches the line size of a second region (and the line size within the first test region matches the line spacing within the second). The horizontally oriented pair of blocks (B and D) is similarly split into a conjugate pair of one light and one dark field and test regions in either of these blocks (B or D) are negative images of the same test region in the block's pair (B or D).

Figure 9:
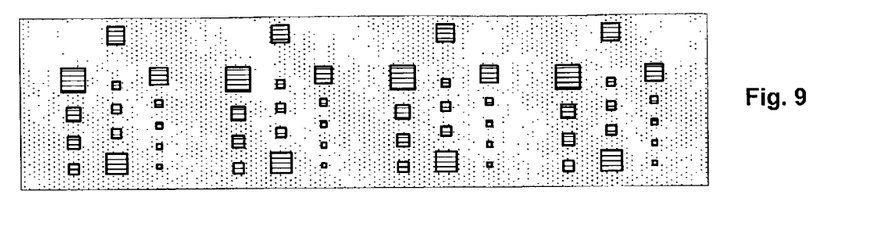
FIG. 9 is a block diagram showing a first background pattern for use within a subset of the panels shown in FIG. 5.
Figure 10:
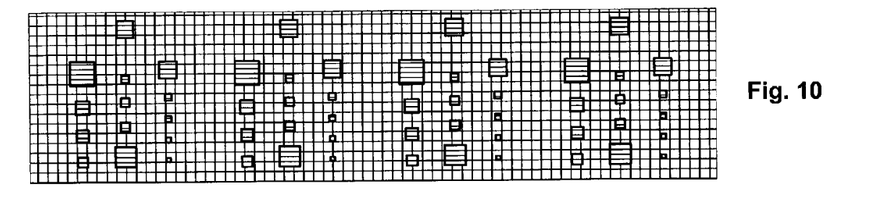
FIG. 10 is a block diagram showing a second background pattern for use within a subset of the panels shown in FIG. 5.

As described, each test region includes the foreground pattern shown in FIG. 7. The panels within inner block E also include a background pattern. As shown in FIG. 9, the background pattern for the panels in inner blocks E1 and E3 is a 2 μm grid with a line width of 0.4 μm. FIG. 10 shows the background pattern for inner blocks E2 and E4. That background pattern is a grid of holes spaced at 1 μm. Each hole has a diameter of 0.2 μm.

Figure 11:
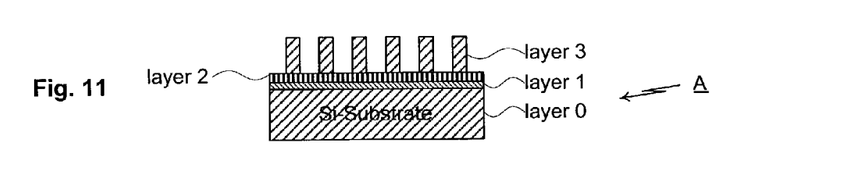
FIG. 11 is a block diagram of a first film stack suitable for creating the standardized sample of the present invention.

Standardized sample 300 is created by etching the surface of a dielectric film to create foreground patterns 700. Depending on the particular application, a wide range of different film stacks may be used for this purpose. One of these is labeled A in FIG. 11. As shown, film stack A includes a number of layers. The first (lowermost) of these (layer 0) is a Silicon substrate. The substrate is followed by a 100A Oxide layer (layer 1), a 500A Nitride layer (layer 2), and 4000A Oxide layer (layer 3). The etching process stops at the bottom of the uppermost layer (layer 3). Film stack A is intended to be easily etchable. The nitride layer (layer 2) provides a robust stop for the etching process (since it etches slowly). The 100A Oxide layer (layer 1) ensures that the Nitride layer (layer 2) is not deposited directly on the Silicon substrate (layer 0).

Figure 12:
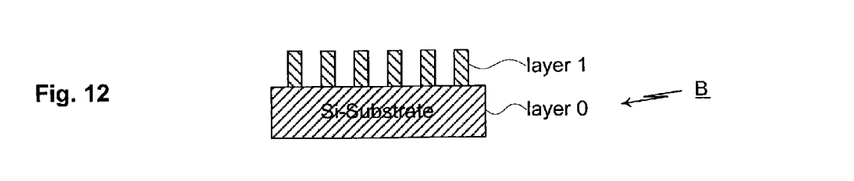
FIG. 12 is a block diagram of a second film stack suitable for creating the standardized sample of the present invention.

A second possible film stack is labeled B in FIG. 12. As shown, film stack B includes two layers. The first of these (layer 0) is a Silicon substrate. The substrate is followed by a 4000 A Oxide (layer 1). This combination (Ox/Si) is used to represent a dielectric etch. The etching process stops at the bottom of the uppermost layer (layer 1). Film stack B is intended to provide a simplified system for characterizing scatterometer performance. The use of two layers means that unnecessary variables and unknowns are eliminated.

Figure 13:
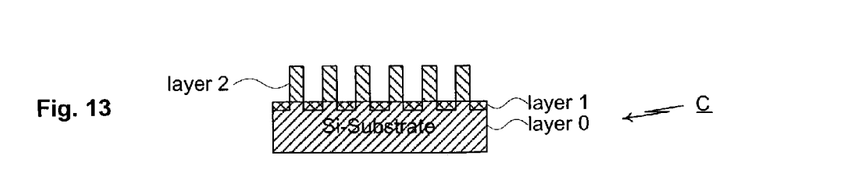
FIG. 13 is a block diagram showing the use of an effective medium to compensate for roughness created during the etching of the film stack of FIG. 12.

In some cases, it is possible that the etching process used to create film stack B will extend beyond the bottom of the uppermost layer (layer 1). FIG. 13 shows a film stack C that exhibits "roughing" of this type. To account for this, the scatterometry model used for film stack C is modified to include an effective medium at the bottom of the trenches formed during the etch process.

Figure 14:
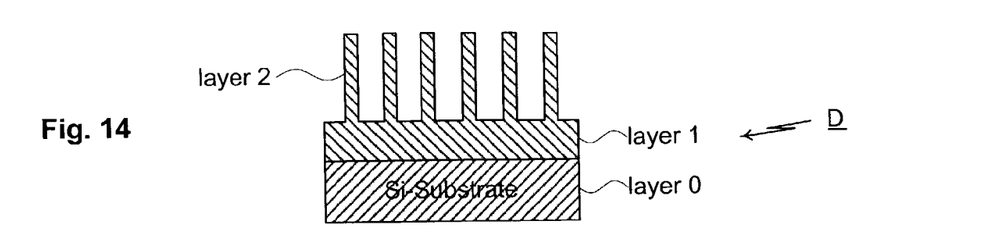
FIG. 14 is a block diagram of a third film stack suitable for creating the standardized sample of the present invention.

FIG. 14 shows a film stack D intended to model deep trenches. As shown, film stack D includes two layers. The first of these (layer 0) is a Silicon substrate. The substrate is followed by a 15000 A Oxide (layer 1). This combination (Ox/Si) is used to represent a dielectric etch. The etching process stops midway through the uppermost layer (layer 1). The use of a thick, partially etched layer makes film stack D an effective model for deep trenches.

Figure 15:
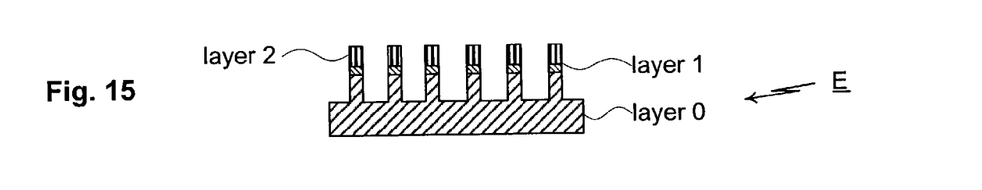
FIG. 15 is a block diagram of a fourth film stack suitable for creating the standardized sample of the present invention.

FIG. 15 shows a film stack E that includes three layers. The first of these (layer 0) is a Silicon substrate. The substrate is followed by a 100 A Oxide layer (layer 1), and a 1500 A Nitride layer (layer 2). This combination (Nitride/Ox/Si) is used to represent Nitride/Ox/Si. The etching process stops midway through the substrate layer (layer 0).

Figure 16:
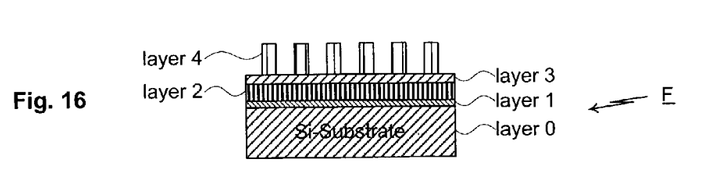
FIG. 16 is a block diagram of a fifth film stack suitable for creating the standardized sample of the present invention.

Film stacks A, B, D and E are relatively simple and include a limited number of layers. To accurately model real-world samples, it is often necessary to include more layers. At the same time, it is generally desirable to avoid the tendency of many layer materials to age or change in response to exposure to light. FIG. 16 shows a film stack F intended to address both of these objectives. Film stack F includes a total of five layers. The first of these (layer 0) is a Silicon substrate. The substrate is followed by a 20 A Oxide layer (layer 1), a 2000 A Poly-Si layer (layer 2), an inorganic ARC (SiOxNy) layer at 193/248 nm (layer 3) and a 3000 A oxide layer (layer 4). The etching process stops at the bottom of the uppermost layer (layer 4). Layer 4 is intended to provide an inorganic substitute for an organic Resist layer. The oxide used in this layer closely models the dielectric response of Resist and is stable over time and exposure to light. Layer 3 is, similarly intended to provide an inorganic and stable substitute for an organic ARC (anti-reflective coating).

Figure 17A:
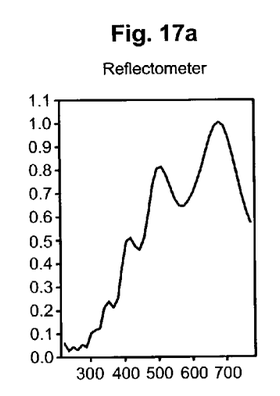
FIGS. 17*a* through 17*e* show simulated spectral responses for the film stack of FIG. 16.
Figure 17B:
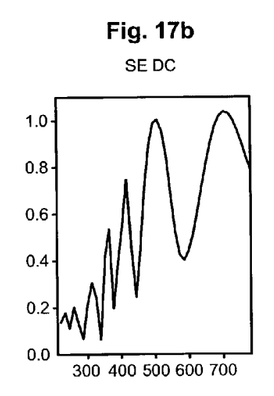
Figure 17C:
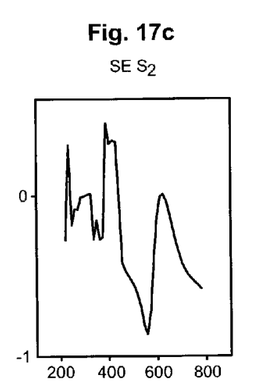
Figure 17D:
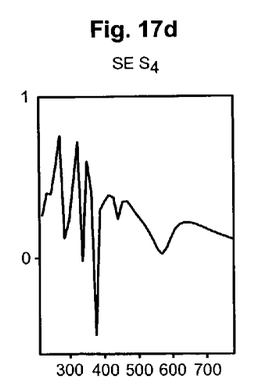
Figure 17E:
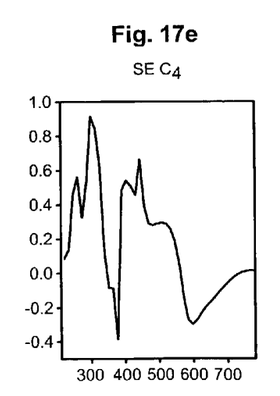

FIG. 17a through 17e show simulated spectral response curves for film stack F. The first figure in this series (FIG. 17a) shows the type of response that would be exhibited by film stack F during inspection by a reflectometer. Each of the following figures is similar, except that the responses correspond to inspection by spectral ellipsometer. In particular, these curves correspond to the response curve of a broadband rotating compensator ellipsometer (RCE) of the type disclosed in U.S. Pat. No. 5,877,859, incorporated herein by reference. In the case of FIG. 17b, the DC signal generated by a spectral ellipsometer is shown. FIGS. 17c and 17d show the sine of the two and four omega signals, respectively. FIG. 17e shows the cosine of the four omega signal.

Figure 18:
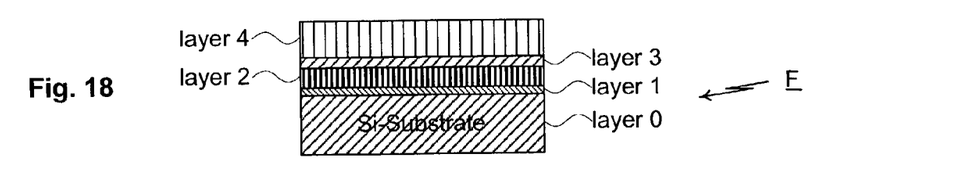
FIG. 18 is a block diagram of an un-etched version of the film stack of FIG. 16.

FIG. 18 shows an un-etched, or pre-etched version of film stack F. Un-etched portions of the film stack can be used to ascertain the dielectric properties of the film stack independently from the diffractive qualities of the gratings within the standardized sample. Un-etched portions (or entirely un-etched film stacks) may also be used for calibration of ellipsometers and reflectometers.

Figure 19A:
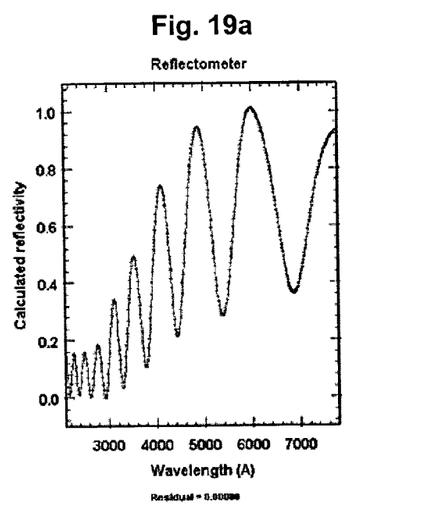
FIGS. 19*a* through 19*d* show simulated spectral responses for the film stack of FIG. 18.
Figure 19B:
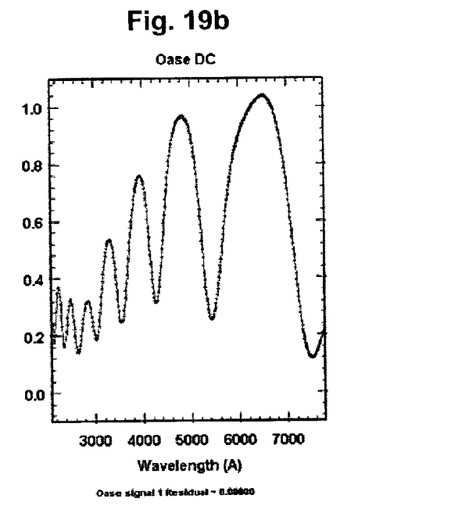
Figure 19C:
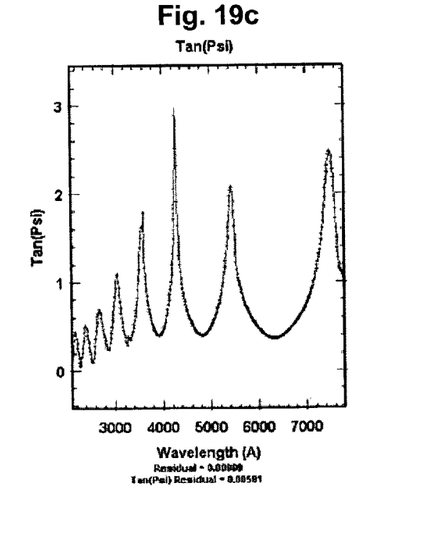
Figure 19D:
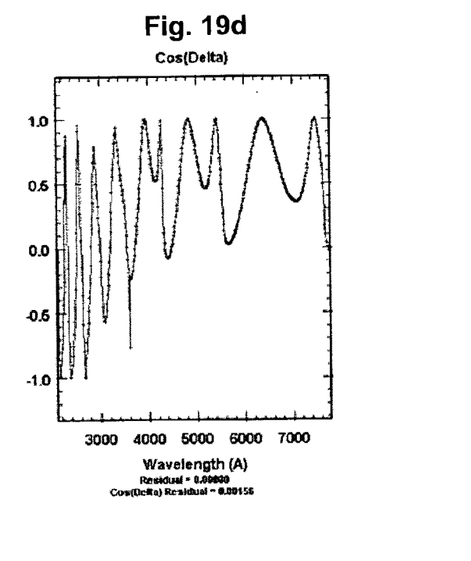

FIG. 19a through 19d show simulated spectral response curves for the un-etched version of film stack F. The first figure in this series (FIG. 19a) shows the type of response that would be exhibited by the un-etched film stack F during inspection by a reflectometer. Each of the following figures is similar, except that the responses correspond to inspection by spectral ellipsometer (RCE). In the case of FIG. 19b, the DC signal generated by an off-axis spectral ellipsometer is shown. FIGS. 19c and 19d are calculations of the conventional ellipsometric parameters tan (psi) and cosine (delta) respectively.

Figure 20:
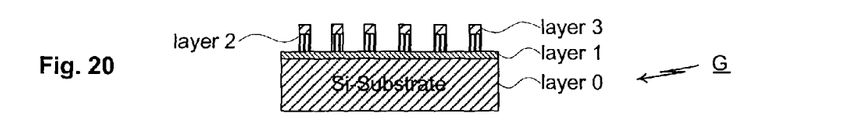
FIG. 20 is a block diagram of a sixth film stack suitable for creating the standardized sample of the present invention.

FIG. 20 shows a second example of a film stack that is both stable and relatively complex. As shown, film stack G includes a total of four layers. The first of these (layer 0) is a Silicon substrate. The substrate is followed by a 20 A Oxide layer (layer 1), a 2000 A Poly-Si layer (layer 2), and an inorganic ARC (SiOxNy) layer at 193/248 nm (layer 3). The etching process stops at the bottom of the top two layers (layers 2 and 3). As described for film stack F, layer 3 is intended to provide an inorganic and stable substitute for an organic ARC (anti-reflective coating).

Figure 21A:
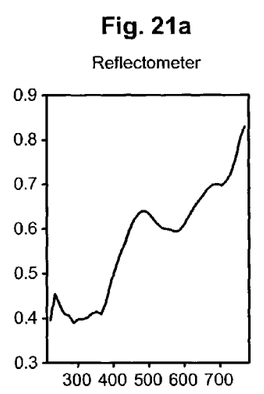
FIGS. 21*a* through 21*e* show simulated spectral responses for the film stack of FIG. 20.
Figure 21B:
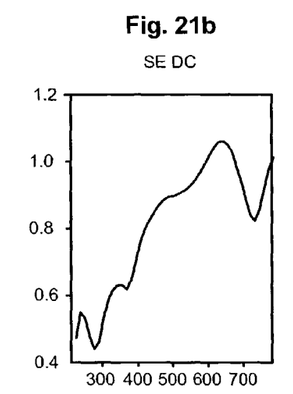
Figure 21C:
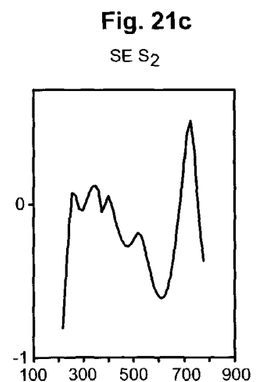
Figure 21D:
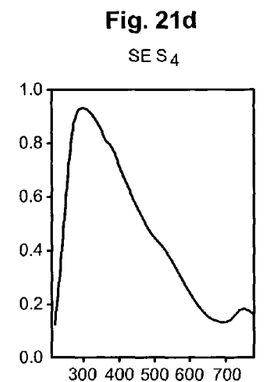
Figure 21E:
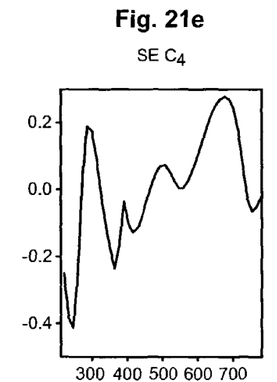

FIG. 21a through 21e show simulated spectral response curves for film stack G. The first figure in this series (FIG. 21a) shows the type of response that would be exhibited by film stack G during inspection by a reflectometer. Each of the following figures is similar, except that the responses correspond to inspection by spectral ellipsometer (RCE). In the case of FIG. 21b, the DC signal generated by a spectral ellipsometer is shown. FIGS. 21c and 21d show the sine of the two and four omega signals, respectively. FIG. 21e shows the cosine of the four omega signal.

Figure 22:
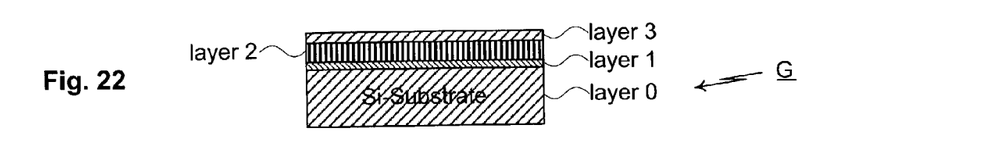
FIG. 22 is a block diagram of an un-etched version of the film stack of FIG. 20.

FIG. 22 shows an un-etched, or pre-etched version of film stack G. Un-etched portions of the film stack can be used to ascertain the dielectric properties of the film stack independently from the diffractive qualities of the gratings within the standardized sample. Un-etched portions (or entirely un-etched film stacks) may also be used for calibration of ellipsometers and reflectometers.

Figures 23A, 23B:
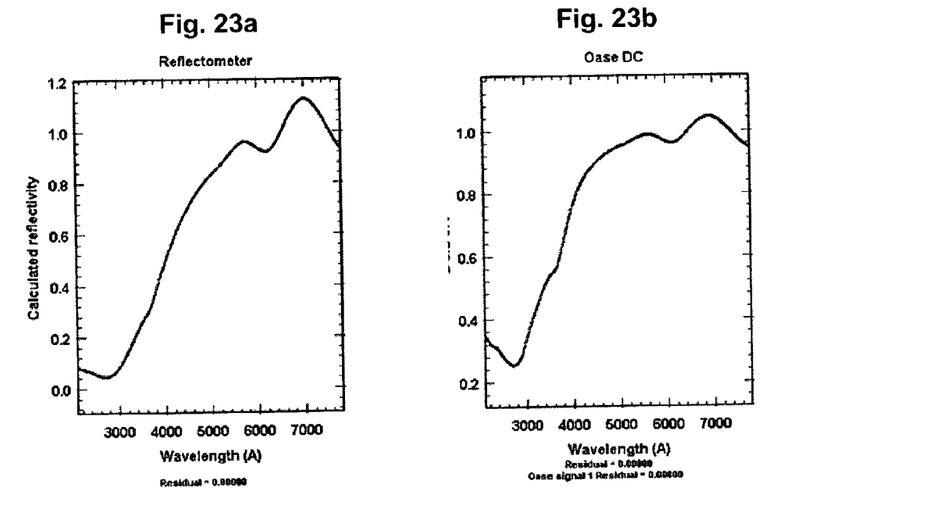
FIGS. 23*a* through 23*d* show simulated spectral responses for the film stack of FIG. 22.
Figures 23C, 23D:
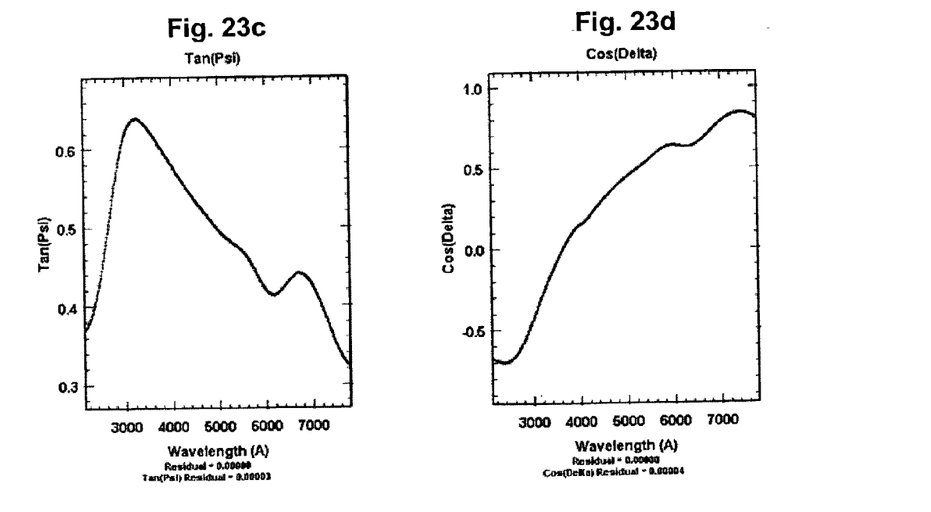

FIG. 23a through 23d show simulated spectral response curves for the un-etched version of film stack G. The first figure in this series (FIG. 23a) shows the type of response that would be exhibited by the un-etched film stack G during inspection by a reflectometer. Each of the following figures is similar, except that the responses correspond to inspection by spectral ellipsometer (RCE). In the case of FIG. 23b, the DC signal generated by an off-axis spectral ellipsometer is shown. FIGS. 23c and 23d show the calculation of tan (psi) and cos(delta) ellipsometric parameters.

Figure 24:
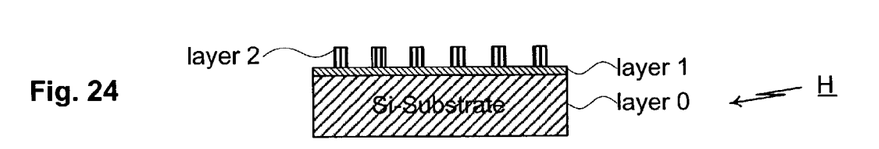
FIG. 24 is a block diagram of a seventh film stack suitable for creating the standardized sample of the present invention.

FIG. 24 shows a third example of a stable film stack. As shown, film stack H includes a total of three layers. The first of these (layer 0) is a Silicon substrate. The substrate is followed by a 20 A Oxide layer (layer 1), and a 2000 A Poly-Si layer (layer 2). This combination (Poly-Si/Ox/Si) is used to represent Poly/Ox/Si. The etching process stops at the bottom of the uppermost layer (layer 2).

Figure 25:
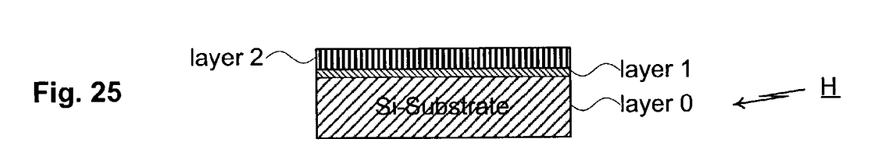
FIG. 25 is a block diagram of an un-etched version of the film stack of FIG. 24.

FIG. 25 shows an un-etched, or pre-etched version of film stack H. Un-etched portions of the film stack can be used to ascertain the dielectric properties of the film stack independently from the diffractive qualities of the gratings within the standardized sample. Un-etched portions (or entirely un-etched film stacks) may also be used for calibration of ellipsometers and reflectometers.

Film stacks F, G and H are examples of a more generalized method for creating stabilized reference film stacks for use in standardized samples and other test samples. Stabilized reference film stacks mimic the dielectric properties of production film stacks without having the tendency to age or change dielectric response when exposed to optical radiation. To create a stabilized reference film stack, the layers within a production film stack are subdivided into two categories. First category layers are the layers that tend to age or change optical response when exposed to optical radiation (chiefly UV radiation). Typically, organic anti-reflective coatings, and organic photo-resistive layers are sensitive to UV radiation and are placed in the first category. Second category layers are the layers within the production film stack that are relatively impervious to aging. Inorganic layers are commonly included in this category.

An effective layer is then defined for each layer included in the first category. Each effective layer is designed to mimic, as closely as possible, the optical response that is exhibited by the corresponding layer in the first category. At the same time, the materials used for the effective layers are selected to be relatively impervious to aging. Each effective layer may include one or more materials in one or more layers. The use of multiple materials and layers is required when the desired combination of optical response and age-resistance is not available or practical using a single material. In general, it should be appreciated that the process of defining effective layers is not perfect and that it is generally not possible to exactly match the dielectric response of the layers in the first category using substitute materials. At the same time it is generally possible to closely approximate the response of first category layers while greatly decreasingly the tendency for the resulting layers to age.

In many cases, the effective layers are selected by substituting an inorganic compound for an aging-prone organic compound. This is particularly true for organic anti-reflective coatings and organic photo resist materials. The effective layers defined for organic anti-reflective coatings are typically fabricated using silicon oxide nitride (SiON). The effective layers for organic photo resist layers are typically fabricated using silicon dioxide ($SiO_2$).

The following tables list organic photo-resist materials and organic anti-reflective coatings for which replacement by inorganic materials may be appropriate:

| Photo resist materials | Manufacturer |
| --- | --- |
| APEX-E ™ | Shipley Company |
| UVIIHS ™, UVIII ™ | |
| UV ™ 82, UV ™ 86, UV ™ 110, UV ™ 113, | |
| UV ™ 135, UV ™ 210 | |
| EPIC ™-S7 | |
| ULTRA-I 123 | |
| AZ ® EXP 5888, 5690S, 5200P, 5400P | AZ Electronic Materia |
| AZ ® DTF ™ 11 | |
| PFR ® IX1060G, PFR ® IX1010G | JSR Microelectronics |
| EIRIS, KRF, ARF series | |
| TDMR, TDQR-IQ, TDUR-P/N series | TOKYO OHKA KOGYO Co., LTD |
| Sumiresist series | Sumitomo Chemical |

| Anti-reflective coatings | Manufacturer |
| --- | --- |
| AR ™2, AR ™3, AR ™8 | Shipley Company |
| AR ™5, AR ™6, AR ™7, AR ™10 | |
| AZ BARLi ® Series | AZ Electronic Materia |

| -continued | |
| --- | --- |
| Anti-reflective coatings | Manufacturer |
| AZ EXP HERB ™ | |
| AZ KrF 3G, AZ KrF 17B | |
| AZ EXP KrF 17G-2 | |
| AZ EXP ArF-1C, ArF-2C, ArF-2P | |
| NFC 540 | JSR Microelectronics |

Once effective layers have been defined, the stabilized film stack may be constructed as a combination that includes the effective layers and replicates the layers from the second category. The overall result mimics the dielectric response of the production film stack without having the tendency to change over time. In general, it should be appreciated that the use of the term "production" is not intended to be limiting. This same method may be used to create stabilized reference film stacks that model the optical response of prototype or proposed film stacks.

What is claimed is:

1. A method for creating a stabilized reference film stack to simulate the optical response of a production film stack, the method comprising:
   subdividing the layers of the production film stack into a first category and a second category, each layer in the first category being characterized by a tendency to experience chemical change upon exposure to optical radiation, each layer in the second category being characterized by a reduced tendency to experience chemical change upon exposure to optical radiation;
   defining an effective layer for each layer in the first category, each effective layer being characterized by a reduced tendency to experience chemical change upon exposure to optical radiation;
   fabricating the stabilized reference film stack as a combination that includes the effective layers and replicas of the layers from the second category.

2. A method as recited in claim 1 wherein at least one of the layers in the first category is formed using an organic material and the corresponding effective layer is formed using one or more inorganic materials.

3. A method as recited in claim 1 wherein at least one of the effective layers is an anti-reflective coating.

4. A method as recited in claim 1 wherein at least one of the effective layers is a photo-resistive coating.

5. A method as recited in claim 1 wherein at least one of the effective layers is formed as a combination of two or more layers.

* * * * *